(12) United States Patent
Pearson et al.

(10) Patent No.: US 6,951,658 B1
(45) Date of Patent: Oct. 4, 2005

(54) EMU-BASED COMPOSITIONS FOR MENTAL WELL-BEING AND METHOD OF USE

(75) Inventors: Maurine Pearson, Pilot Point, TX (US); Teresa Leigh Barr, Port Townsend, WA (US)

(73) Assignee: Pearson Research & Development Limited, Pilot Point, TX (US)

( * ) Notice: Subject to any disclaimer, the term of this patent is extended or adjusted under 35 U.S.C. 154(b) by 0 days.

(21) Appl. No.: 10/614,925

(22) Filed: Jul. 8, 2003

(51) Int. Cl.[7] .................. A61K 35/12; A61K 35/55; A61K 9/70; A61K 45/00
(52) U.S. Cl. .................. 424/520; 424/283.1; 424/400; 424/449; 424/682
(58) Field of Search .................. 424/520, 283.1, 424/400, 449, 682

(56) References Cited

U.S. PATENT DOCUMENTS

| | | | |
|---|---|---|---|
| 4,753,964 A | 6/1988 | Horrobin | 514/558 |
| 4,933,354 A * | 6/1990 | Ikeguchi et al. | 514/343 |
| 5,431,924 A | 7/1995 | Ghosh | 424/522 |
| 5,432,199 A | 7/1995 | Cavazza | 514/546 |
| 5,468,776 A * | 11/1995 | Yehuda | 514/560 |
| 5,472,713 A | 12/1995 | Fein | 424/522 |
| 5,556,847 A | 9/1996 | Johnson | 514/178 |
| 5,624,898 A | 4/1997 | Frey, II | 514/12 |
| 5,662,921 A | 9/1997 | Fein | 424/436 |
| 5,693,614 A * | 12/1997 | Torii et al. | 514/12 |
| 5,958,384 A | 9/1999 | Holick | 424/60 |
| 6,036,973 A | 3/2000 | Guittard | 424/457 |
| 6,127,370 A * | 10/2000 | Smith et al. | 514/250 |

FOREIGN PATENT DOCUMENTS

| | | | |
|---|---|---|---|
| JP | 04049235 | 2/1992 | A61K/31/20 |
| JP | 08231391 | 9/1996 | A61K/31/20 |
| WO | WO 98/33474 | 1/1997 | A61K/7/40 |

* cited by examiner

*Primary Examiner*—Leon B. Lankford, Jr.
*Assistant Examiner*—Ruth A. Davis
(74) *Attorney, Agent, or Firm*—Buskop Law Group, P.C.; Wendy Buskop

(57) ABSTRACT

The invention is a method and supplement for treatment of symptoms of Alzheimer's disease, dementia, depression, and combination thereof, comprising: from about 20 wt % to about 70 wt % emu oil, wherein the emu oil further comprises from about 1 wt % to about 12 wt % linolenic acid; from about 5 wt % to about 30 wt % l-arginine; from about 5 wt % to about 30 wt % pyroglutamate; from about 0.5. wt % to about 20 wt % B-12 methylcobalamin; and from about 0.5 wt % to about 20 wt % calcium, wherein the supplement is adapted for crossing a blood brain barrier, and for fortification of phospholipids in neurotransmitters of a brain to increase cell proliferation for treatment of symptoms of Alzheimer's disease, dementia, depression, and combinations thereof.

8 Claims, No Drawings

EMU-BASED COMPOSITIONS FOR MENTAL WELL-BEING AND METHOD OF USE

FIELD OF INVENTION

The invention relates to a supplement and method for treating Alzheimer's disease, dementia, manic depression, and bi-polar disease that is an alternative to commercial antidepressants. The supplement transdermally absorbs for crossing a blood brain barrier, and for fortification of phospholipids in neurotransmitters of a brain to increase cell proliferation

BACKGROUND OF THE INVENTION

The present application is a continuation of co-pending U.S. patent application Ser. No 09/915,470, filed in the United States Patent and Trademark Office on Jul. 26, 2001, which claims priority from abandoned U.S. Provisional Patent Application Ser. No 60/262,578, filed in the United States Patent and Trademark Office on Jan. 18, 2001.

Found in the wild only in Australia, Emus are the second largest members of the ratite group of flightless birds in the world. The emu have wings but they are very tiny. They can run up to 35–40 miles an hour, as they have very large and strong legs. Although a very docile creature, the emu's legs are so strong; one kick can break a man's leg. Now Emus are being farmed in many parts of the world. They are raised for their valuable products, which include very low fat meat, supple leather hides, decorative and nutritional eggs, and very rich oil, which are obtained from the emu. Emus are by nature, very healthy and immune to many diseases. Emus are referred to a "living dinosaurs," as their skeletal structure closely resembles some dinosaurs. Emus living today closely resemble their ancestors of millions of years ago.

Emu oil, a food by product, is obtained from the fat of the Emu. It is an all-natural substance. When processed, the fat is taken through a series of steps to refine, sterilize and deodorize the oil. Not all Emu oil on the market is refined. Some Emu oil is simply rendered, which means the oil is simply filtered, and may contain contaminants. Emu oil contains high amounts of EFA's (essential fatty acids). EFA's produce energy in the process of oxidation. In humans EFA's govern growth, vitality and mental state of mind. Oxidation is the central and most important living process in our body.

Emu oil by nature is not regarded as a sterile ingredient. Due to lack of regulatory controls and procedures, emu oil is processed in many different ways, i.e., some forms of rendering, which is simply a filtration process, which leaves the emu oil with its natural yellow color, and a slight odor. The present invention uses a refinement process, which yields a clearly pure emu oil product, creamy white and odor free. The present invention utilizes a sterilization technique to render the emu oil in the present invention free of contaminants to be used as a preparation and treatment via oral ingestion, topical transdermal delivery systems, application to mucous membranes such as intranasal passages and the like.

U.S. Pat. No. 5,958,384 teaches that topical or parenteral administration of emu oil to a mammal stimulates the proliferation of skin, as well as rejuvenating photo-damaged skin. This same patent teaches that emu oil also stimulates melannogenesis in the skin and it can be used to treat disorders such as hypo-pigmentation.

Emu oil is a well-known anti-inflammatory. For years, emu oil has been shown to relieve inflammation in the muscles tissues and joints both externally as well as internally. It is a surprising and novel aspect of the present invention that an oil from an oil from an animal source could have such an impact on human and animal health.

The Aboriginal peoples of Australia have reportedly used emu oil for centuries for the treatment of skin conditions and muscle and joint pain. More recently, emu oil has been reported to have a variety of uses, including treatment of bruised, burned and dry skin tissue, and as a moisturizer in cosmetic preparations. U.S. Pat. No. 5,472,713 discloses a variety of uses for emu oil, including lowering cholesterol, trigylceride and low density lipoproteins, increasing high density lipoproteins, and improving growth and condition of nails. Topical application of emu oil is disclosed for treatment and prevention of allergies, nosebleeds, headaches and scarring. U.S. Pat. No. 5,431,924 discloses an anti-inflammatory composition containing an emu oil component. The '924 patent discloses that emu oil exhibits dermal absorption, but that a transport enhancer such as isopropyl alcohol or eucalyptus oil is necessary to achieve anti-inflammatory effect by topical administration. An emu trade association publication (Emu Today and Tomorrow, October 1994, at 15) reports that the oil is penetrating, emulsifying, non-comedogenic and non-irritating, and further that a product containing emu oil and alpha-hydroxy acid is under development.

U.S. Pat. No. 5,662,921 discusses how emu oil is therapeutically used in methods for lowering cholesterol, triglycerides and low density lipoproteins and increasing high density lipoproteins; and in general lowering serum cholesterol in the blood and is hereby incorporated by reference.

PCT/AU91/00517 it was found that the remarkable anti-inflammatory effects of the emu oil composition, when mixed with a miscible diluent, disappeared upon removal of the yellow components of the emu oil. Accordingly, PCT/AU91/00517 is directed to using specifically the yellow component of the emu oil along with a miscible diluent. However, the present inventors have found upon refining emu oil to remove the yellow color and reduce its odor, there is no difference in the constituents of the oil, besides its impurities being removed, and the refined oil can be used according to the present invention. Accordingly, for the uses of emu oil in accordance with the present invention either the raw yellow oil or refined oil can be used.

Even so, a need has long existed for a formula, using emu oil which can be used in hospitals, as a sterile formula for oral ingestion alone or as a carrier fluid for other drugs and vitamins, topical transdermal delivery systems, and the like, in clinical environments while remaining stable and usable over time without degradation.

SUMMARY OF THE INVENTION

The present invention is a supplement for treatment of symptoms of Alzheimer's disease, dementia, depression, and combination thereof. The supplement is made of emu oil, L-arginine, pyroglutamate, B-12 methylcobalamin, and calcium. The emu oil includes linolenic acid. The supplement is adapted for crossing a blood brain barrier and for fortification of phospholipids in neurotransmitters of a brain to increase cell proliferation for treatment of symptoms of Alzheimer's disease, dementia, depression, and combinations thereof.

The invention is also a method for treatment of symptoms of Alzheimer's disease, dementia, manic depression, bi-polar disease and combinations thereof. The method involves preparing a supplement and administering the supplement to a patient. The supplement is adapted for crossing a blood brain barrier, and for fortification of phospholipids in neurotransmitters of a brain to increase cell proliferation for treatment of symptoms of Alzheimer's disease, dementia, depression, and combinations thereof.

The invention can be in the form of a topical composition, an injestable composition, and an injectable composition, or applied using a bandage, patch or similar elastomeric patch.

DETAILED DESCRIPTION OF THE PREFERRED EMBODIMENTS

Before explaining the present invention in detail, it is to be understood that the invention is not limited to the particular embodiments herein and it can be practiced or carried out in various ways.

The present invention is a supplement for treatment of symptoms of Alzheimer's disease, dementia, manic depression, and bi-polar disease.

The present invention is a Emu oil based formulated composition that has transdermal properties, both internal and external thus creating healthier cells within the bodies of humans and animals that proliferate at an accelerated rate, while feeding and maintaining cell health with the emu oil composition. The invention absorbs quickly in the gut and intestines, releasing into the bloodstream and crossing the blood brain barrier, reducing inflammation that can cause damage to the neurons, increases cell proliferation, increasing the bodies ability to maintain and regenerate cells, thereby becoming an effective treatment as a cognitive enhancer for Alzheimer's disease, dementia and depression related disorders such as depression and bi-polar disease while having the unexpected effect of lowering LDL cholesterol.

The invention has a preferred formula containing

Emu oil—20–70 wt %;

L-Arginine—5–30 wt %;

Pyroglutamate—5–30 wt %;

B-12 Methylcobalamin—0.5–20wt %; and

Calcium—0.5–20wt %.

In an alternative embodiment, the present invention has the form of an external transdermal delivery system that can be used with or without an elastomeric device. The formula with the having the external transdermal delivery system includes Emu oil—20–70 wt %;

L-Arginine—5–30 wt %;

Pyroglutamate—5–30 wt %;

B-12 Methylcobalamin—0.5–20wt %; and

Calcium—0.5–20 wt %.

In an alternative embodiment, the present invention can be in the form of a nutritional supplement for having a positive effect on serum cholesterol. The formula having a positive effect on serum cholesterol has Emu oil—20–70 wt %;

L-Arginine—5–30 wt %;

Pyroglutamate—5–30 wt %;

B-12 Methylcobalamin—0.5–2 wt %; and

Calcium—0.5–2 wt %.

Other vitamins are contemplated to be used within the scope of the present invention.

These vitamins include Vitamin C and Vitamin E.

The emu oil that is most preferred in this invention has the following chemical analysis:

| | |
|---|---|
| Free fatty Acid | 0.02% |
| Peroxide Value | 0.3 units |
| Moisture | 0.02% |
| Calculated Iodine Value | 72.8 mEq/100 g |
| OSI | 11.95 Hours @ 110.0 degrees C. |

The fatty acid composition of emu oil with respect to human skin oil is as follows:

| | Emu Oil | Human Skin Oil |
|---|---|---|
| Myristic C:14:0 | 0.3% | 2.1% |
| Palmitic C:16:0 | 20.3% | 20.2% |
| Palmitoleic C:16:1 | 3.2% | 3.8% |
| Margaric C:17:0 | 0.2% | |
| Margaric oleic C:17:1 | 0.1% | |
| Stearic C:18:0 | 10.1% | 11.2% |
| Oleic C:18:1 | 51.6% | 30.8% |
| Linoleic C:18:2 | 13.1% | 15.1% |
| Linolenic C:18:3 | 0.5% | 0.3% |
| Arachidic C:20:0 | 0.1% | |
| Eicosinoac C:20:1 | 0.5% | |

Other fatty acids contemplate4d by the invention include elaidic and vaccenic.

An analysis of fatty acids in emu oil reveals that the oil contains approximately 70% unsaturated fatty acids. The major fatty acid found in emu oil is oleic acid, which is monosaturated and which comprises over 40% of the total fatty acid content. Emu oil also contains both of the two EFA's which are important to human health. 20% linolenic, and 1–2% alpha-linolenic acid, which are also known as octodocenic acids. It is a surprising a novel aspect of the present invention that the emu oil in the emu oil composition has a naturally occurring odd-numbered carbon molecule known as margaric acid C17:0, and margaric oleic acid C17:1. Most odd-numbered carbon molecules are synthesized. It is a surprising and novel aspect of the present invention that the emu oil in the composition is unique as it is naturally derived and is not in opposition with the gate-keepers of the blood brain barrier.

The blood-brain barrier maintains a homeostatic environment in the central nervous system. The capillaries that supply the blood to the brain have tight junctions which block passage of most molecules through the capillary endothelial membranes. While the membranes do allow passage of lipid soluble materials, such as heroin and other psychoactive drugs, water-soluble materials such as glucose, proteins and amino acids do not pass through the blood-brain barrier. Therefore, it is a surprising and novel aspect of the present invention that the transdermal abilities of the odd-numbered carbon molecule naturally inherent to the emu oil along with the synergistic effect of the amino acid L-arginine and pyroglutamate act together to cross the blood-brain barrier via the central nervous system and therefore fortify and maintain cell and neuron health.

The method and composition of the present invention therefore provides for delivery to the central nervous system of compounds that are necessary for treatment modalities in any condition affecting the central nervous system where the blood-brain barrier would impede the delivery of the compound. The method and composition of the present invention is an improvement of currently available means of delivery of compounds to the central nervous system through the blood-brain barrier, such as oral ingestion, direct topical application to the skin and mucous membranes. Also the application can be made using a patch, such as an elastomeric bandage with the application placed on it.

A surprising and novel feature of the emu oil is unique unsaturated fat molecules, as most land animals have a higher concentration of saturated fats. Typical fat contains both saturated and unsaturated fatty acids. The fats found in land animals have a higher percentage of side chains than do the fats in sea animals. Although unsaturated fats are less efficient storage sites for food energy because they have fewer CH bonds than do saturated fats, they have a distinct advantage for animals that live in cold water. Saturated fats melt at higher temperatures than do unsaturated fats. In cold waters, sea animals with solid fats would have the reduced ability to move. This theory also subject to analysis, and may be proven easier to transport unsaturated fats through the skin structure and membrane into the lipid layer for release into the central nervous system and blood-brain barrier, rather than a saturated fat, as well as quickly absorbed by the gut, to be transported to the body.

Essential fatty acids (EFA's) play two important roles in human physiology. Both derive from their incorporation into the phospholipids of cell membranes. By virtue of their high degree of unsaturation, and, hence low melting points, they decrease membrane viscosity and affect several aspects of membrane function. Nearly all cells contain basic fat and oil substances. Fats are called energy storehouses, as on a weight-by-weight basis, they contain twice as much energy as a carbohydrate or protein. Fatty acids are also natural blood thinners; they can prevent blood clots, which can lead to heart attack and stroke. Essential fatty acids are also known to contain natural anti-inflammatory compounds. The emu oil in the emu oil composition contains natural essential fatty acids, which are from a natural source and non-toxic.

The present invention, when topically applied is seen to increase the synthesis of DNA in the epidermis, which is a measure of increase in the proliferative activity of the dermis. It is contemplated that the presence of Oleic acid, a simple triglyceride which contains only one type of fatty acid (oleic acid) enables the present invention to work effectively. Naturally occurring triglycerides usually are mixed triglycerides; i.e., they contain more than one fatty acid. An example of a mixed triglyceride is palmmitodiolein, the fatty acid composition of which is, as the name indicates, one molecule of palmitic acid and two molecules of oleic acid. This triglyceride may have structural arrangements and the fatty acid molecules may be arranged with palmitic acid occupying any of the two possible different positions. Oleic acid is also a monosaturated fat. When these fatty acid molecules are combined with a stearic acid molecule, they create an odd-numbered carbon atom, which has a transdermal effect internally or externally in the bodies of human and animals, thereby transporting beneficial nutrients across the tight junctions of the blood brain barrier to fortify cells naturally, without toxicity.

Essential fatty acids are essential polyunsaturated fatty acids. Fatty acid deficiencies such as linoleic acid deficiency symptoms include scaly skin and slow to heal wounds. Linoleic acid is required for the formation and maintenance of the epidermal barrier. The present invention requires essential fatty acids.

Essential fatty acids containing and odd-numbered carbon atom are essential and crucial to fortify neurons and transport beneficial ingredients to the neurotransmitters in the brain and strengthen and rebuild the cells by increasing essential fatty acids as well as amino acid content through the central nervous system and crossing the blood brain barrier, thus allowing and enhancing new cell and membrane proliferation, as well as transporting beneficial vitamin, nutrients and drugs through the tight junctions of the blood brain barrier and to the cell of the neurons.

Stearic acid is also known as octadecanoic acid, one of the most common long chain fatty acids, found in combined form in natural animal and vegetable fats. Commercial stearic acid is a mixture of approximately equal amounts of stearic and palmitic acids and small amounts of oleic acid. This in turn is also an odd-numbered carbon atom which is naturally occurring in the emu oil of the composition. In nature stearic acid occurs primarily as a mixed triglyceride, or fat, with other long-chain acids and as an ester of fatty alcohol. It is much more abundant in animal fat than in vegetable fat; lard and tallow often contain up to 30 percent stearic acid. Stearic acid is a component of a preferred formulation of the present invention.

The composition and structure of the fatty acids of the naturally occurring lipids have an even number of carbon atoms because they are synthesized from acetyl groups, each of which contains two carbon atoms. Fatty acids with 16 (palmitic acid) and 18 (stearic acid) carbon atoms are most commonly found in nature. Fatty acids constitute important components of lipids in plants, animals and microorganisms. In most cases, they are not found in free form, but instead are bound to other compounds to form fatty acid containing lipid, e.g., neutral lipids (triglycerides) sterols, phosphoglycerides such as lecithin, and sphingolipids such as sphingomyelin.

Two typical fatty acids are oleic and palmitic. Although palmitic acid and stearic acid are the major saturated fatty acids found in animal and plant tissues, significant amounts of other saturated fatty acids such as myristic acid and lauric acid, occur in certain tissues, and lignoceric acid and behenic acid also are found in high concentrations in healthy brain sphingolipids and neurofibulatroy tangles. Amounts of fatty acids with an odd number of carbon atoms are also known, e.g., pentadecanoic acid and heptadeconoic acid. The present invention emu oil composition contains high amounts of octadecanoic acid, pentadecanoic acid and heptadeconoic acid. Naturally occurring heptadocenic acid is normally isolated in mutton and shark liver oil, and is naturally occurring and as well present in high amounts in the emu oil.

Over the past few decades, Alzheimer's disease has emerged from obscurity. Once considered a rare disorder, it is now recognized as a major public health problem having a severe impact on millions of Americans and their families. Alzheimer's disease is one of the most common causes of the loss of mental function known broadly as dementia. This type of dementia proceeds in stages, gradually destroying memory, reason, judgment, language, and eventually the ability to carry out even the simplest of tasks. These characteristic symptoms acquired a name in the early part of the 20th century when Alois Alzheimer, a German physician, described the signs of the disease in the brain. Alzheimer had a patient in her fifties who suffered from what seemed to be a mental illness. But when she died in 1906, an autopsy revealed dense deposits, now called neuritic plaques, outside and around the nerve cells in her brain. Inside the cells were twisted strands of fiber, or neurofibrillary tangles.

Currently, a definite diagnosis of Alzheimer's disease is still only possible when an autopsy reveals these hallmarks of the disease. Plaques and tangles remained mysterious substances until the 1980's, when neuroscientists discovered the proteins that make up these telltale anomalies. As research progresses, it is turning up clues to how plaques and tangles develop and how they relate to other changes in the brain. We now know that Alzheimer's begins in the entorhinal cortex and proceeds to the hippocampus, a way station important in memory formation. It then gradually spreads to other regions, particularly the cerebral cortex. This is the outer area of the brain, which is involved in functions such as language and reason. In the regions attacked by Alzheimer's, the nerve cells or neurons degenerate, losing their connections or synapses with other neurons. Some neurons die.

The cerebral cortex is involved in conscious thought and language; the basal forebrain, which has large numbers of neurons containing acetylcholine, a chemical important in memory and learning; the hippocampus, which is essential to memory storage; neuritic plaques; and neurofibrillary tangles. Alzheimer's disease attacks nerve cells or neurons in several regions of the brain. The earliest signs of Alzheimer's are found in the nearby entorhinal cortex. Hallmarks of Alzheimer's disease include neuritic plaques or outside neurons, and neurofibrillary tangles inside neurons. As the hippocampal neurons degenerate, short-term memory falters. Often the ability to perform routine tasks begins to deteriorate as well. Disturbing behaviors, such as wandering and agitation, beset many people as the disease progresses. In its final stages Alzheimer's disease wipes out the ability to recognize even close family members or to communicate in any way. All sense of self seems to vanish, and the individual becomes completely dependent on others for care. Patients often live for years with this condition, dying eventually from pneumonia or other diseases. The duration of Alzheimer's disease from time of diagnosis to death can be 20 years or more. The average length is thought to be in the range of 4 to 8 years.

An estimated four million people living in the United States have Alzheimer's disease. Most surveys have found the percentage of people age 85 and older who have any kind of dementia, including Alzheimer's, to be in the range of 25 to 35 percent. One study in Boston, however, found that the percentage of people with Alzheimer's disease alone was 47.2 percent in people age 85 and over. One problem in getting accurate figures lies in the lack of a single definition of either dementia or Alzheimer's disease. If current population trends continue and no cure is found, the actual number of people with the disease could double every 20 years.

The cost of caring for a person with Alzheimer's disease is extremely high, the government covers an estimated $4.4 billion dollars per year, and states cover an additional $4.1 billion per year. Most of the remaining costs fall on the patient and their family. Caring for a patient with Alzheimer's disease costs more than $47,000 a year whether the person lives at home or in a nursing home, according to a study in northern California.

In addition, the composition can be used to treat for inflammation of the brain tissue and a method has been developed to use one of the embodiments of the invention for depression, including manic depression or alternatively, bi polar disease.

The brain has hundreds of billions of neurons, any one of which can have thousands, even hundreds of thousands, of connections with other neurons. Within and among their extensive branches travel dozens of chemical messengers; neurotransmitters, hormones, growth factors, and more, linking each neuron with others in a vast communications network. Somewhere in this complex signaling system lies the cause of Alzheimer's disease. In the past two decades, neuroscientists have combed through it in search of defects that might explain what goes wrong in this disease. One of their earliest findings came from studies of neurotransmitters, the chemicals that relay messages between neurons.

Neurotransmitters reside in tiny sacs at the ends of axons, the long tube-like extensions of neurons. Released when electrical impulses pass along the axon, the chemicals cross a minute space called the synapse and bind to a molecule or receptor sitting in the membrane of the next neuron. The neurotransmitters then either break down or pass back into the first neuron, while other substances inside the second neuron take up and relay the message. In the mid 1970's, scientists discovered that levels of a neurotransmitter called acetylcholine fell sharply in people with Alzheimer's disease. The discovery was intriguing for several reasons. Acetylcholine is a critical neurotransmitter in the process of forming memories. Moreover, it is the neurotransmitter used commonly by neurons in the hippocampus and cerebral cortex—regions devastated by Alzheimer's disease. Since that early discovery, which was one of the first to link Alzheimer's disease with biochemical changes in the brain, acetylcholine has been the focus of hundreds of studies.

Scientists have found that its levels fall somewhat in normal aging and the loss of hormones, such as estrogen, testosterone and human growth hormone, but drop by about 90 percent in people with Alzheimer's disease. They have turned up evidence linking this decline to memory impairment. And they have looked for ways to boost its levels as a possible treatment for Alzheimer's disease. Other neurotransmitters have also been implicated in Alzheimer's disease. For example, serotonin, somatostatin, and noradrenaline levels are lower than normal in some Alzheimer's patients, and deficits in these substances may contribute to sensory disturbances, aggressive behavior, and neuron death.

Most neurotransmitter research, however, continues to focus on acetylcholine and the loss of hormones because of its steep decline in Alzheimer's disease and its close ties to memory formation and reasoning.

Once the message carried by a neurotransmitter has crossed the synapse it passes into another territory, where neuroscientists are beginning to find more clues to Alzheimer's disease. The gateways to this new territory are the receptors, coil-shaped proteins embedded in neuron membranes. First, these molecules have chemical bonds with molecules of fat, called phospholipids that lie next to them in the membrane. Phospholipids are polar compounds. Polar compounds carry an electrical charge at one end. Several studies have detected phospholipid abnormalities in neurons affected by Alzheimer's disease.

These abnormalities might change the behavior of neighboring receptors and garble the message as it passes from neuron to neuron. Several genes associated with Alzheimer's disease have an impact on one or more of these systems. They may create problems for the vasculature, in the metabolism of cholesterol or in the synthesis of proteins. For example, the mutations in chromosomes 21, 14 and 1 have an impact on how proteins are synthesized. Alzheimer's also causes changes in the immune system. It elicits inflammatory reactions, producing toxins that kill cells. Nonsteroidal anti-inflammatories may work for just this reason, because they block that process. The natural nonsteroidal anti-inflammatory properties of the emu oil composition are also non-toxic and can cross the blood brain barrier to help overcome the symptoms of Alzheimers, dementia and mood imbalance.

Secretagogues are substances that stimulate the endocrine system to increase hormonal secretions. There are two peptide hormones that act together to increase or decrease HGH output from the pituitary gland. These hormones are Somatostatin and Growth Hormone-Releasing Hormone Growth hormones are essential substances produced in the body that help repair and maintain muscle tissue, and support proper body function. Deficiencies in growth hormones may result in fatigue, impaired cognition, muscle weakness, and emotional imbalance.

And finally, the endocrine system, which secretes hormones directly into the bloodstream, plays a significant role in the impact and possible treatment of Alzheimer's disease. There are at least two classes of hormones that affect Alzheimer's disease. One is a corticoid steroid, the stress hormones that play an important role in energetics. In excessive amounts it kills cells and it kills cells precisely in the same area where Alzheimer's pathology occurs. For women, estrogen is the other important hormone involved. In addition to regulating the reproductive cycle, it has a tremendous impact on how the nervous system repairs itself. It has a synergistic interaction with the neurotrophins, a class of chemicals involved in repair systems and in cell reproduction. Estrogen proves one of the most promising areas of drug treatments.

The role of estrogen in maintaining health has been receiving increasing attention in health reports. Recent studies, including one published in August in The Lancet, reported a link between the loss of estrogen and cognitive decline. However, it could be that elevated levels of two other hormones FSH and LH are more important as a factor in the development of Alzheimer's disease.

The synergistic effect of the L-arginine, pyroglutamate and emu oil in the present invention acts as a secretagogue as it naturally helps maintain ones own natural hormonal levels.

Second, researchers have uncovered several types of receptors for acetylcholine and are now exploring their different effects on message transmission. It may be that the shapes and actions of the receptors themselves, independent of their neighboring phospholipids, play a role in Alzheimer's.

But the receptor is just the starting point of the cell's communications system. When a neurotransmitter binds to a receptor, it triggers a cascade of biochemical interactions that relay the message to the neuron's nucleus, where it activates certain genes, or to the end of the axon, where it passes to other cells. This messaging system involves a number of proteins, and abnormalities in these proteins or dysfunction at the relay points could block or garble the message. So could other events and processes in the cell, such as problems with the system that turns food into energy (metabolism) or the mechanisms that keep calcium levels in balance. Drug therapies aimed at these various postsynaptic events are now being explored, although most are still in the very earliest phases of testing. Several proposed treatments for Alzheimer's hinge on the theory that free-radical damage plays a key role in the disease and that antioxidants, therefore, should be able to slow down its progression.

A free radical is a molecule with an unpaired electron in its outer shell. Ordinarily an oxygen molecule, like other molecules, has an even number of electrons in orbit. But the normal process of turning food into energy metabolism produces oxygen radicals with an odd number of electrons. The oxygen radical is extremely reactive; it will latch readily onto another molecule a part of the membrane or a unit of DNA, for instance. When this happens, it can set off a chain reaction, releasing chemicals that can be harmful to the cell. Scientists theorize that damage from oxygen radicals plays a role in aging as well as in diseases ranging from glaucoma to cancer. In Alzheimer's disease, free radicals are suspects for several reasons. They attack phospholipids, the molecules of fat in neuron membranes. All molecules contain amounts of fat in cell membranes. Some researchers hypothesize that free radicals upset the delicate membrane machinery that regulates what goes into and out of a cell, such as calcium.

Calcium is a novel aspect is a component of the present invention. Calcium is the mineral in your body that makes up your bones and keeps them strong. Ninety-nine percent of the calcium in your body is stored in your bones and teeth. The remaining 1% is in your blood and soft tissues and is essential for life and health. Without this tiny 1% of calcium, your muscles wouldn't contract correctly, your blood wouldn't clot and your nerves wouldn't carry messages. Cells of the central nervous system possess many different types of calcium channels. Voltage-dependent calcium channels are involved in many neuronal functions, including synaptic transmission between neurons. The present invention utilizes calcium selected from the group; calcium citrate, calcium carbonate, calcium gluconate, calcium lactate, coral calcium, calcium hydroxyapatite, Methylcobalamin or vitamin B-12 is the only form of B-12 used by the central nervous system. The body normally converts cyanocobalamin, or regular B-12, into methylcobalamin for use by the nervous system. Methylcobalamin has a significant, positive, neurological effect with no known toxicity. Methylcobalamin is considered a methyl donor. It donates methyl groups to the myelin sheaths that insulate nerves, maintaining integrity, and helps regenerate damaged neurons. The present invention utilizes vitamin B-12 Methylcobalamin as a necessary component.

The discovery that the neurotransmitter acetylcholine declines in Alzheimer's disease led naturally to the hypothesis that replacing acetylcholine could stop the disease. Since that finding, many scientists have looked for compounds that can increase the levels of acetylcholine, replace it, or slow its breakdown. This search has taken them into a broader territory that includes the cells that use acetylcholine and the enzymes and other proteins that take part in its manufacture or activity; a grouping known as the cholinergic system. The cholinergic system includes the neurons that contain acetylcholine and the neurons and proteins that are stimulated or activated by acetylcholine.

The body can synthesize many building blocks and uses amino acids to help this function. Protein is extremely versatile in structure as well as function and is the building block of tissue and muscle mass. It also serves as the chemical catalysts driving reactions within the body. Every protein in your body is made up of some combination of around twenty amino acids. A protein is a chain of many amino acids. The structural versatility in proteins is due to the fact that any given protein may have as many as 130 amino acids linked one by one together. This means that there are 13020 different combinations of amino acids possible. This means that there are about 1,900,000,000,000, 000,000,000,000,000,000,000,000,000,000 different proteins that could be made, each serving a potentially different function. This is what makes proteins one of the most versatile structurally complicated molecules known. The body needs to have access to all the amino acids in order to synthesize the proteins and can synthesize about 10–12 of the twenty amino acids that it needs. The main essential nutrients that the body needs are essential amino acids, essential fatty acids, vitamins, and minerals.

Pyroglutamate (also called 2-oxo-pyrrolidone carboxylic acid, or PCA) is an amino acid naturally occurring in vegetables, fruits, dairy products, and meat, and seems to be an important flavor constituent in these foods. It is also normally present in large amounts in the human brain, cerebrospinal fluid, and blood. Pyroglutamate is known to have a number of remarkable cognitive-enhancing effects. After oral administration, pyroglutamate passes into the brain through the blood-brain barrier and stimulates cognitive functions. Pyroglutamate improves memory and learning in rats, and has anti-anxiety effects in rats (Pearson and Shaw, 1988). Pyroglutamate has also been shown to be effective in alcohol-induced memory deficits in humans (Sinforiani, 1985) and, more recently, in people affected with multi-infarct dementia (Scoppa, in press). In these patients, the administration of pyroglutamate brought about a significant increase of attention and an improvement on psychological tests investigating short-term retrieval, long-term retrieval, and long-term storage of memory. A statistically significant improvement was observed also in the consolidation of memory. In human subjects, pyroglutamate was compared with placebo in a randomized double-blind trial for assessing its efficacy in treating memory deficits in 40 aged subjects. Twenty subjects were treated with pyroglutamate and 20 with placebo over a period of 60 days. Memory functions were evaluated at baseline and after 60 days of treatment by means of a battery made up of six memory tasks. The results show that pyroglutamate is effective in improving verbal memory functions in subjects affected by age-related memory decline.

Some people use arginine, a single amino acid that causes the pituitary gland to release one's own natural growth hormone. Arginine pyroglutamate, in addition to having cognitive enhancing effects, is an excellent growth hormone releaser because it is carried more efficiently across the blood-brain barrier than L-arginine alone.

Some people suffering from ailments such as diabetes and HIV may notice unpleasant side effects from the combination of L-arginine and pyroglutamate. A novel and surprising aspect of the present invention that the emu oil neutralizes and buffers any adverse effects.

Most amino acids, with the exception of glycine, can appear in two forms called the D- and L-forms. Each form is a reversed mirror image of the other. Amino acids in the L-form are the natural form of amino acids found in living plant and animal tissues, and are considered to be more compatible to human biochemistry than the D-forms, with the exception of D-phenylalanine, which is beneficial. All amino acids used in human protein structures are of the L-form, with the exception of phenylalanine, which can also appear as DL-phenylalanine.

L-Arginine, also just called Arginine, has appeared in many products of the past couple of years, gaining popularity as a nonprescription treatment for high cholesterol L-arginine is a non-essential amino acid which is abundant in protamines and histones, these are proteins associated with nucleic acids.

L-arginine is found in: whole-wheat, rice, nuts, seeds, corn, soy, grapes, coco, carob and some other foods. It can be purchased from pharmacies. L-Arginine having the chemical composition of $C6-H14-N4-O2$ Health food and vitamin stores also offer various products containing pyroglutamate. Arginine pyroglutamate (one source of pyroglutamate) is often used for its growth-hormone releasing effect, but is still effective as a cognitive enhancer in this form. Other names for Pyroglutamate include Alpha-aminoglutaric acid lactam, Glutamic acid lactam, Glutimic acid, Glutiminic acid, PyroGlu, Pyroglutamic acid. Other names for Arginine Pyroglutamate include Adjuvant, Piraglutargine, and Arginine Pidolate.

A combination teaching L-arginine and pyroglutamate U.S. Pat. No. 4,388,325 Orzalesi Jun. 14, 1983 and is hereby incorporated as reference. Orzalesi teaches L-arginine D,L-pyroglutamate has a tonic activity at the neuro-endocrinal level with a specific effect in enhancing sexual behavior of Mammalia males, particularly in individuals of elderly age, humans being included.

While substances pass easily from the bloodstream to cells in other parts of the body, the brain has a complex set of defenses that protect it from possible poisons. Known as the blood-brain barrier, these defenses include physical barriers, which can be described as tightly opposed cells in the walls of the blood vessels. Another defense is chemical; enzymes that act as gatekeepers, escorting only certain substances into the inner compartments.

The present invention of the emu oil composition is another way to cross the blood brain barrier to deliver drugs, nutrients and supplements to the neurons and act as a carrier fluid.

The present invention includes linoleic acid and linolenic acid and which when transferred to the lipid layer may be crucial to "feeding" cells, thereby creating more energy for cells to burn, thus enhancing membrane cell proliferation and fortification, Linoleic acid and linolenic acid is required for the formation and maintenance cells and of the epidermal barrier.

The present invention is contemplated as a sterile formulation. The guidance on validation of the manufacture of sterile products can be found in the FDA's submission Documentation for Sterilization Process Validation for Human and Veterinary Drug Products (November 1994), which is hereby incorporated by reference.

It is conceived that this formula can be modified to that it is prepared in the form of a gel, a cream, a lotion, a spray, a patch, or an enhanced oil.

Information regarding the use of fatty acids and certain natural oils for lowering cholesterol and treating conditions related to cholesterol metabolism, including, but not limited to, dosages of fatty acids and fat emulsions and forms of administration, are known to those with skill in the art as illustrated by the United States Patents Incorporated herein by reference. The following United States patents are incorporated herein by reference: Winitz U.S. Pat. No. 3,849,554; DiTuio U.S. Pat. No. 3,969,508; Iwamura U.S. Pat. No. 4,472,432; Revici U.S. Pat. No. 4,513,008; Burger U.S. Pat. No. 4,603,142; Ward U.S. Pat. No. 4,678,808; Revici U.S. Pat. No. 4,851,437, Beyer U.S. Pat. Nos. 4,920,123 and 5,110,817; Berger U.S. Pat. No. 4,999,380; Wakabayashi U.S. Pat. No. 5,034,414; Hidvegi U.S. Pat. No. 5,277,910; Mattson U.S. Pat. No. 4,034,083, reissue No. 33,885 and Jandacek U.S. Pat. No. 4,005,195, reissue No. 33,996, regarding the information referred to in the preceding sentence and the subject matter encompassed by these patents.

The present invention is a supplement for treatment of symptoms of Alzheimer's disease, dementia, manic depression, and bi-polar disease and as a surprising and novel aspect naturally lowers the bad cholesterol, or low density lipoprotein [LDL] cholesterol −25%. Serum cholesterol is a major risk factor for heart disease and the leading cause of death in the U.S. Cholesterol lowering drugs are the major pharmaceutical products sold. A product that could naturally reduce serum cholesterol levels without pharmaceutical drugs would be beneficial. The composition is made of given weight percents of emu oil, L-arginine, pyroglutamate, B-12 methylcobalamin, and calcium. The emu oil further includes a naturally occurring linolenic and linoleic acids, which are intrinsic to the emu oil. The supplement is adapted for absorbing into the gut, entering the central nervous system, thereby crossing the blood brain barrier, thereby fortifying the phospholipids in neurotransmitters of a brain to increase cell proliferation for treatment of symptoms of Alzheimer's disease, dementia, manic depression, and bi-polar disease, while reducing overall cholesterol levels.

Examples 1 and 2 illustrates the cholesterol lowering effects of daily ingestion of emu oil. As can be seen from Examples 1 and 2, emu oil is effective for lowering blood serum cholesterol. The patients in both Examples 1 and 2 have found the effectiveness of emu oil is greatest when it is taken on a regular basis and that the effectiveness of the emu oil for lowering cholesterol diminishes when emu oil is not taken on a regular basis.

Example 1—Mature human female aged 38 years ingests approximately 5 drops or one teaspoon of emu oil per day: Prior to this patient's ingestion of emu oil, testing on Jan. 6, 1993 yielded the following results:

| Total cholesterol | 272 mg/dl |
| LDL | 193 mg/dl |
| HDL | 58 mg/dl |
| Triglycerides | 103 mg/dl |

Subsequent to ingestion of emu oil, testing yielded the following results: Testing on Feb. 19, 1994, when patient was taking approximately one teaspoon of emu oil per day, but not on a regular basis:

| Total cholesterol | 231 mg/dl |
| HDL | 43 mg/dl |
| Chol./HDL | 5 mg/dl |
| LDL | 171 mg/dl |
| Triglycerides | 87 mg/dl |

Testing on May 26, 1994, when patient was taking approximately one teaspoon of emu oil per day on a more regular basis:

| Total cholesterol | 210 mg/dl |
| LDL | 132 mg/dl |
| HDL | 66 mg/dl |
| Triglycerides | 58 mg/dl |

Example 2 Mature human female aged 60 years ingests 7 to 10 drops of emu oil per day, approximately one teaspoonful. Patient has previously taken Mevocore for lowering her cholesterol and has suffered side effects, including hair loss. Patient does not suffer from side effects from ingesting emu oil and her hair has been restored.

Prior to this patient's ingestion of emu oil, testing on Jul. 27, 1993 yielded the following results:

| Total cholesterol | 292 mg/dl |
| HDL | 40 mg/dl |
| Chol./HDL | 7.3 |
| LDL | 205 mg/dl |
| Triglycerides | 233 mg/dl |

Subsequent to ingestion of emu oil of approximately one teaspoon per day, testing on Feb. 2, 1994 yielded the following results:

| Total cholesterol | 264 mg/dl |
| HDL | 38 mg/dl |
| Chol./HDL | 7 |
| LDL | 179 mg/dl |
| Triglycerides | 239 mg/dl |

Externally the formula can be a topical preparations or in various parenteral preparations. Externally the formula can also be applied as a trandermal delivery system with or without an elastomeric device, such as the "patch" or applied to nasal passages, as well as ingested orally.

The formula of this invention uniquely can be sterilized. Traditionally, sterilization has broken down the components of oils which contain these types of fatty acids. The objective of a sterilization process is to remove or destroy all microorganisms in or on a preparation and to assure in this way the preparation is free of infectious hazards when used with a patient. Since the variety and amounts of the variety and amounts of sterile materials required for health care have increased in significant proportions, sterilization technology has become increasingly important.

The best formula for the present invention has the following components. The ranges for each component are in weight percent of the entire composition The invention may be embodied in many forms without departing from the spirit or essential characteristics of the invention.

While this invention has been described with emphasis on the preferred embodiments, it should be understood that within the scope of the appended claims the invention might be practiced other than as specifically described herein.

What is claimed is:

1. A method for treating inflammation of brain tissue associated with Alzheimer's disease, dementia, depression, and combinations thereof, comprising the steps of:

a. preparing a supplement comprising:
      i. from about 20 wt % to about 70 wt % emu oil, wherein the emu oil further comprises from about 1 wt % to about 12 wt % linolenic acid;
      ii. from about 5 wt % to about 30 wt % l-arginine;
      iii. from about 5 wt % to about 30 wt % pyroglutamate;
      iv. from about 0.5 wt % to about 20 wt % B-12 methylcobalamin; and
      v. from about 0.5 wt % to about 20 wt % calcium;

b. administering the supplement to a patient, wherein the supplement reduces inflammation of brain tissue and fortifies phospholipids in neurotransmitters to increase cell poliferation for treatment of symptoms of Alzheimer's disease, dementia, depression, and combinations thereof.

2. The method of claim 1, further comprising adding as an additional component up to 10 wt % linolenic acid.

3. The method of claim 1, further comprising adding as an additional component between 0.5 to 20 wt % Vitamin E.

4. The method of claim 1, further comprising adding as an additional component between 0.5 to 20 wt % Vitamin C.

5. The method of claim 1, wherein the supplement is an ingestible dosage.

6. The method of claim 1, wherein administering the supplement is by a transdermal delivery system.

7. The method of claim 1, wherein administering the supplement is by application to mucous membranes.

8. The method of claim 1, wherein administering the supplement is by applying an at least partially adhesive elastomeric patch on the skin.

* * * * *